(12) United States Patent
Howard et al.

(10) Patent No.: US 6,562,859 B1
(45) Date of Patent: May 13, 2003

(54) UREIDO DERIVATIVES OF POLY-4-AMINO-2-CARBOXY-1-METHYL PYRROLE COMPOUNDS FOR INHIBITION OF INFLAMMATION

(75) Inventors: O. M. Zack Howard, Frederick, MD (US); Joost J. Oppenheim, Bethesda, MD (US); William J. Murphy, Frederick, MD (US); Edward A. Sausville, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/555,733

(22) PCT Filed: Dec. 4, 1998

(86) PCT No.: PCT/US98/25811

§ 371 (c)(1),
(2), (4) Date: Aug. 4, 2000

(87) PCT Pub. No.: WO99/27939

PCT Pub. Date: Jun. 10, 1999

Related U.S. Application Data

(60) Provisional application No. 60/067,526, filed on Dec. 4, 1997.

(51) Int. Cl.[7] ................................................. A61K 31/40
(52) U.S. Cl. ........................................ 514/422; 514/518
(58) Field of Search .................................. 514/422, 518

(56) References Cited

U.S. PATENT DOCUMENTS

| | | | |
|---|---|---|---|
| 5,260,329 A | 11/1993 | Mongelli et al. | 514/422 |
| 5,420,296 A | 5/1995 | Mongelli et al. | 548/518 |
| 5,534,539 A | 7/1996 | Mongelli et al. | 514/422 |
| 5,593,976 A | 1/1997 | Mongelli et al. | 514/48 |
| 5,596,105 A | 1/1997 | Mongelli et al. | 548/518 |
| 5,656,644 A | 8/1997 | Adams et al. | 514/341 |

FOREIGN PATENT DOCUMENTS

| | | | |
|---|---|---|---|
| GB | 2310207 | | 8/1997 |
| IT | WO-91/10649 A1 | * | 7/1991 |
| WO | WO 91/10649 | | 7/1991 |
| WO | WO 95/23806 | | 9/1995 |
| WO | WO 97/28796 | | 8/1997 |

OTHER PUBLICATIONS

Clanton et al., *Antiviral Research*, 27, 335–354 (Aug., 1995).
Howard et al., *Trends in Biotech*, 14, 46–51 (Feb., 1996).
Howard O.M.Z., Grimm M., Tarasova N.J., Murphy W., Hollingshead M.G., Turpin J.A., Rice W.G., Oppenheim J.J., *Ureido Analog of Distamycin Blocks Chemokine Receptor Mediated Function* (Month Undeterminable, 1997).

* cited by examiner

*Primary Examiner*—Dwayne C. Jones
(74) *Attorney, Agent, or Firm*—Leydig, Voit & Mayer, Ltd.

(57) ABSTRACT

A method of using a ureido derivative of a poly-4-amino-2-carboxy-1-methyl pyrrole or a pharmaceutically acceptable salt thereof to inhibit inflammation, particularly non-TNF-α dependent inflammation, in a mammal.

23 Claims, No Drawings

UREIDO DERIVATIVES OF POLY-4-AMINO-2-CARBOXY-1-METHYL PYRROLE COMPOUNDS FOR INHIBITION OF INFLAMMATION

CROSS REFERENCE TO RELATED APPLICATIONS

This application is the U.S. national phase of International Patent Application PCT/US98/25811, which was filed Dec. 4, 1998, and claims priority under 35 U.S.C. §119(e) to U.S. provisional Patent Application No. 60/067,526 which was filed Dec. 4, 1997, and has since lapsed.

TECHNICAL FIELD OF THE INVENTION

The present invention relates to inhibition of inflammation by administration of a pharmacologically active ureido derivative of poly-4-amino-2-carboxy-1-methyl pyrrole.

BACKGROUND OF THE INVENTION

Inflammatory reactions are serious medical indications arising from a variety of conditions. Essential to the early inflammatory response is the selective recruitment of leukocytes into the affected tissue(s). This process is controlled, in part, by chemokines, which are small (8–10 kD), inducible cytokines that act primarily as chemoattractants and activators of specific types of leukocytes in a variety of immune and inflammatory responses (Oppenheim et al., *Ann. Rev. Immunol.*, 9, 617–648 (1991); and Taub et al., *Cytokine*, 5, 175–179 (1993)). Chemokines are produced in response to an array of factors, including viruses, bacterial products, IL-1, TNF, C5a, LTB4, and IFNs (Strieter et al., *J. Immunol.* 156, 3583–3586 (1996)). Chemokines have been detected during inflammation in the skin, brain, joints, meninges, lungs, blood vessels, kidneys, and gastrointestinal tract. Within these organs, chemokines have been identified in many types of cells, indicating that most cells secrete chemokines given the appropriate stimulus.

Chemokines have been subdivided into families based on the arrangement of the conserved cysteine residues of the mature proteins (Baggiolini et al., *Adv. Immunol.*, 55, 97–179 (1994); and Baggiolini et al., *Ann. Rev. Immunol.*, 15, 675–705 (1997). The α- and β-chemokines, which contain four conserved cysteines, belong to the largest families. The CXC or α-chemokines are those which have one amino acid residue separating the first two conserved cysteine residues, whereas the CC or β-chemokines are those in which the first two conserved cysteine residues are adjacent. Additionally, there are at least two other families, including the C or γ-chemokines, which lack two (the first and third) of the four cysteine residues (Kelner et al., *Science*, 266, 1395–1359 (1994)), and the CXXXC chemokines, in which the first two cysteine residues are separated by three amino acids (Bazan et al. *Nature*, 385, 640–644 (1997)).

Within the CXC or α-chemokine family, there are chemokines that contain a characteristic glutamic acid-leucine-arginine (ELR) sequence immediately preceding the first cysteine residue near the N terminus and those that lack this sequence (Clark-Lewis et al., *J. Biol. Chem.*, 266, 23128–23134 (1991)). CXC chemokines possessing the ELR sequence (e.g., human IL-8, mouse KC, mouse MIP-2, mouse LIV, ENA-78, GCP-2, and GROα, β and γ) are chemoattractants and activators of neutrophils, whereas CXC chemokines lacking the sequence (e.g., IP10/mouse CRG, PBSF/SDF-1, and PF4) act primarily on lymphocyte populations. The CC or β-chemokines (e.g., MIP-1α, MIP-1β, HCC-1, LEC, TARC, Eotaxin and RANTES) and the C or γ-chemokines (e.g., Lymphotactin) chemoattract and activate monocytes, lymphocytes, dendritic cells, eosinophils, and basophils with variable selectivity.

Chemokines mediate their chemotactic and other activities by binding to specific G-protein-coupled cell-surface receptors on target cells (Premack et al., *Nat. Med.*, 2, 1174–1178 (1996); and Murphy et al., *Ann. Rev. Immunol*, 12, 593–633 (1994)). Like other G-protein-coupled receptors, chemokine receptors are functionally linked to phospholipases through G proteins and receptor activation leads to, among other things, the generation of inositol triphosphate, the release of intracellular calcium, and the activation of protein kinase C (Lodi et al., *Science*, 263, 1762–1767 (1994)). To date, five human CXC chemokine receptors (CXCR1 through CXCR5), eight human CC chemokine receptors (CCR1 through CCR8), and one human CXXXC chemokine receptor ($CX_3CR1$) have been identified. While some receptors are restricted to certain cell types, others are widely expressed on a variety of cells. Further, chemokine receptors may be constitutively expressed on some cells and inducible on others, and may also be sensitive to the state of cell activation and differentiation. Finally, some chemokine receptors are also expressed on nonhematopoietic cells, including neurons, astrocytes, epithelial cells, and endothelial cells, suggesting further roles for the chemokine system.

Additionally, recent work has shown that some viral genomes are capable of encoding chemokine and chemokine receptor homologues (Gao et al., *J. Biol. Chem.*, 269, 28539–28542 (1994); and Ahuja et al., *J. Biol. Chem.*, 268, 20691–20694 (1993)). For example, the open reading frame (ORF) US28 of the human Cytomegalovirus (CMV) encodes a protein that shares approximately 30% sequence homology with the CC chemokine receptor CCR-1 and is capable of binding the MIP-1α, MIP-1β, MCP-1 and RANTES chemokines in vitro. Similarly, the ORF ECRF3 of *Herpes saimiri* encodes a protein that is 30% homologous with the IL-8 chemokine receptors and able to bind IL-8, GRO-α, GRO-β and NAP-2 chemokines. Other human herpesviruses (HHV) also have been shown to express chemokine-receptor homologues that can bind human chemokines (Luster, *New Engl. J. Med.*, 338, 436–445 (1998); Soldan et al., *Nature Med.*, 3, 1394–1397 (1997); and Wells et al., *TIPS*, 19, 376–379 (1998)). For example, Kaposi's sarcoma-associated HHV8 expresses receptor homologues that cause the infected cell to respond to CXC chemokines, such as IL-8, SDF-1α and IP10. The HHV6 virus, which has been found in nervous system tissue characterized by the active myelin destruction associated with multiple sclerosis (Soldan (1997), supra), encodes a β-chemokine receptor that is capable of binding MIP-1α, MIP-1β, RANTES, and MCP-1 chemokines (Isegawa et al., *J. Vir.*, 72, 6104–6112 (1998)). Significantly, in contrast to other viruses, such as the HIV-1 virus, which infects its host's cells via the host's chemokine receptors, the herpesviruses enter their host's cells via the Pol receptor. Once the herpesvirus gains entry into the cell, it produces virally encoded chemokines and chemokine receptors, which are effectively masked from the host cell's immune system.

The secretion of chemokines has been detected in a wide variety of diseases characterized by inflammatory reactions resulting from the selective accumulation and activation of leukocytes in the affected tissue(s) (see Strieter (1996), supra). The type of inflammatory infiltrate that characterizes a specific disease is controlled, in part, by the type of chemokines expressed in the diseased tissue. For example, patients with acute respiratory distress syndrome, which is characterized by a massive influx of neutrophils into the tissue, exhibit an elevated concentration of potent neutrophil chemoattractants. Recently, it has been shown that IL-8 production is also increased in reperfusion injury, which similarly involves the recruitment and activation of neutrophils (Strieter (1996), supra; and Karakurum et al., *J. Clin. Invest.*, 93, 1564–1570 (1994)). Patients suffering from asthma demonstrate a selective accumulation and activation of eosinophils in lung tissue, correlating with an elevated level of Eotaxin, RANTES, and MIP-1α. Similarly, monocyte chemoattractant proteins play an important role in allergic inflammation, which is also characterized by the activation and migration of eosinophils into the affected tissue(s). Other disease states associated with inflammatory responses mediated through chemokines include arthritis, non-bacteria-mediated respiratory distress syndrome, and blunt force trauma, as well as the demyelination of nerve cells associated with multiple sclerosis.

Those skilled in the art will appreciate that prior art methods of alleviating or mitigating the negative effects of inflammation are limited. This presents a serious problem for those patients who can not tolerate current available medications, such as aspirin, which is used to treat blunt force trauma, or anti-inflammatory agents, which are used to treat allergies. Accordingly, there is a need for new methods of lessening inflammation, in particular non-TNF-dependent inflammation.

Ureido derivatives of substituted pyrroles, a class of compounds regarded as Distamycin A derivatives, are known to inhibit angiogenesis and HIV replication. For example, see U.S. Pat. No. 5,420,296 (Mongelli et al.) and Clanton et al., *Antiviral Research*, 27, 335–354 (1995). Additionally, it has been suggested that some of these compounds might be used to treat a disease state in which TNF-α plays a detrimental role in the pathology (see U.S. Pat. No. 5,260,329 (Mongelli et al.)). Surprisingly, it has now been discovered that the dimeric ureido derivatives of poly-4-amino-2-carboxy-1-methyl pyrrole are useful for inhibiting inflammation, in particular non-TNF-α dependent inflammation.

In view of this, it is an object of the present invention to provide a method of inhibiting inflammation, in particular inflammation that is not mediated by TNF-α. This and other objects and advantages of the present invention will become apparent front the description provided herein.

SUMMARY OF THE INVENTION

The present invention provides a method of inhibiting inflammation, particularly non-TNF-α dependent inflammation, by administering an inflammation-inhibiting effective amount of a ureido derivative of a substituted pyrrole of the formula (I):

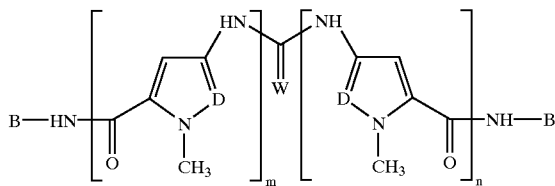

wherein m and n are the same and each is an integer of 1 to 6; W is oxygen or sulphur; each of the B groups, which need not be, but preferably are the same, is (a) a saturated or an unsaturated carbocyclic ring system substituted by one or more acid groups (b) a saturated or an unsaturated, heteromonocyclic or heteropolycyclic ring, containing one or more heteroatoms chosen from nitrogen, oxygen, and sulfur, substituted by one or more acid groups; (c) a pyranyl or furanyl sugar residue substituted by one or more acid groups; or (d) a —CH$_2$(CHA)$_r$CH$_2$A group, wherein each A group, being the same or different, is an acid group and r is 0, 1 or 2; each occurrence of D is independently selected and is N or CH; or a pharmaceutically acceptable salt thereof. Upon administration of the compound or a pharmaceutically acceptable salt thereof, the inflammation is inhibited.

DETAILED DESCRIPTION OF THE INVENTION

The present invention provides a method of inhibiting inflammation, in particular non-TNF-α dependent inflammation, by administering to a mammal in need thereof (or at risk of developing an indication advantageously treated by reduction of inflammation) an inflammation-inhibiting effective amount of a compound of the formula (I):

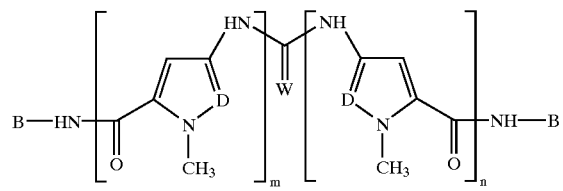

wherein m and n are the same and each is an integer of 1 to 6, and preferably an integer of 2 to 4; W is oxygen or sulphur; each occurrence of D is independently selected and is N or CH; each of the B groups, which need not be the same, but preferably are the same, is
  (a) a saturated or an unsaturated carbocyclic ring system substituted by one or more acid groups;
  (b) a saturated or an unsaturated, heteromonocyclic or heteropolycyclic ring, containing one or more heteroatoms chosen from nitrogen, oxygen, and sulfur, substituted by one or more acid groups;
  (c) a pyranyl or furanyl sugar residue substituted by one or more acid groups; or
  (d) a —CH$_2$(CHA)$_r$CH$_2$A group, wherein each A group, being the same or different, is an acid group and r is 0, 1 or 2; or a pharmaceutically acceptable salt thereof, whereupon administration of the compound or a pharmaceutically acceptable salt thereof to the mammal, the inflammation is inhibited.

When two or more acid groups are present on a B group, as defined above under (a), (b) and (c), they can be the same or different. Examples of acid groups according to the definition of a B group given above under (a), (b), (c) and (d) for instance can be those chosen from the group consisting of sulfonic, sulfuric, sulfamic, sulfinic, phosphoric, phosphonic, phosphamic and carboxylic acid groups, i.e. SO$_3$H, SO$_4$H, SO$_3$NH$_2$, SO$_2$H, PO$_4$H$_2$, PO$_3$H$_2$, PO$_2$NH$_3$ and CO$_2$H. Preferably the are selected from the group consisting of sulfonic, sulfinic, phosphonic, phosphamic, and carboxylic acid groups.

Preferably, B is as defined above under (a). Preferably, when B is as defined above under (a), (b) and (c), it is substituted by 1 to 3 acid groups. When B is as defined above under (a) and (b), preferably it has 1 to 5 rings, and more preferably 1 to 3 rings. The rings defined under (a) and (b) preferably have 4 to 10 ring atoms, more preferably 5 to 8 ring atoms, and most preferably 5 or 6 ring atoms in each ring. Additionally, the rings of the ring system are preferably fused, as in naphthalene. Aromatic examples of B, defined above under (a), include phenyl, naphthyl, indenyl, anthracenyl, phenanthrenyl, benzonaphthyl, and fluorenyl. When B is a ring as defined above under (b) it is, for example, tetrahydropyranyl, tetrahydrofuranyl, furanyl, thiophenyl, pyrrol, oxazolyl, indenyl, benzofuranyl, benzopyronyl, quinolinyl, purinyl, or pyrimidinyl. Preferably, B is naphthyl. Preferably, the naphthyl is substituted with 1, 2 or 3 acid groups selected from sulfonic acid and phosphonic acid. When B is a sugar residue, as defined above under (c), it is, for example, a residue derived from glucosyl or ribosyl. When B is a group as defined above under (d), r is preferably 2.

Examples of pharmaceutically acceptable salts are either those with inorganic bases, such as sodium, potassium, calcium and aluminium hydroxides, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines.

Preferred compounds according to the present invention include the compounds of formula (I), wherein: each of m and n, being the same, is 2–4; W is oxygen; the B groups are the same and each is (a') an unsaturated carbocyclic ring system substituted by 1 to 3 acid groups; (b') a tetrahydropyranyl or tetrahydrofuranyl ring substituted by 1 to 3 acid groups; or (c') a glucosefuranosyl residue substituted by 1 to 3 acid groups; and the pharmaceutically acceptable salts thereof.

Some specific examples of preferred compounds useful in the context of the invention are the following:

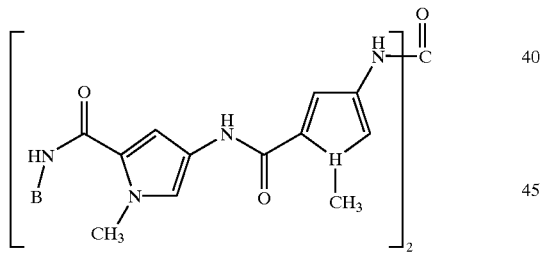

wherein B is:

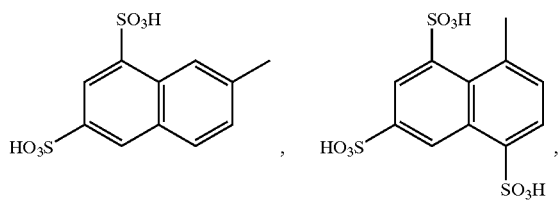

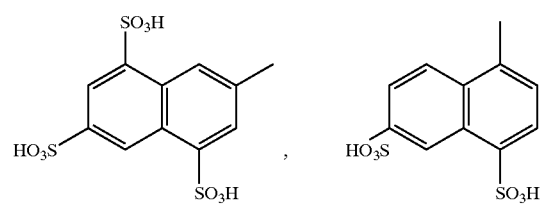

(also known as NSC 651016),

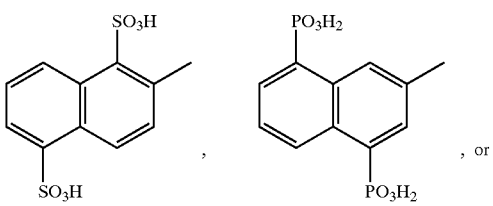

, or

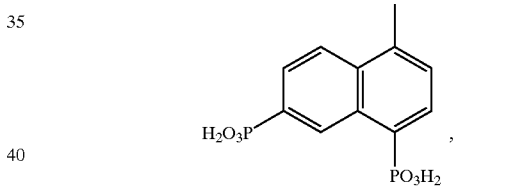

, and the pharmaceutically acceptable salts thereof.

Other preferred compounds for use in the present inventive method include:

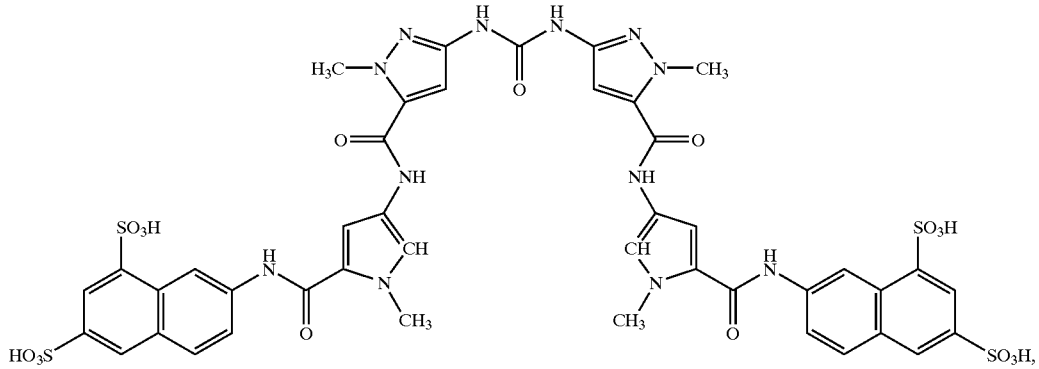

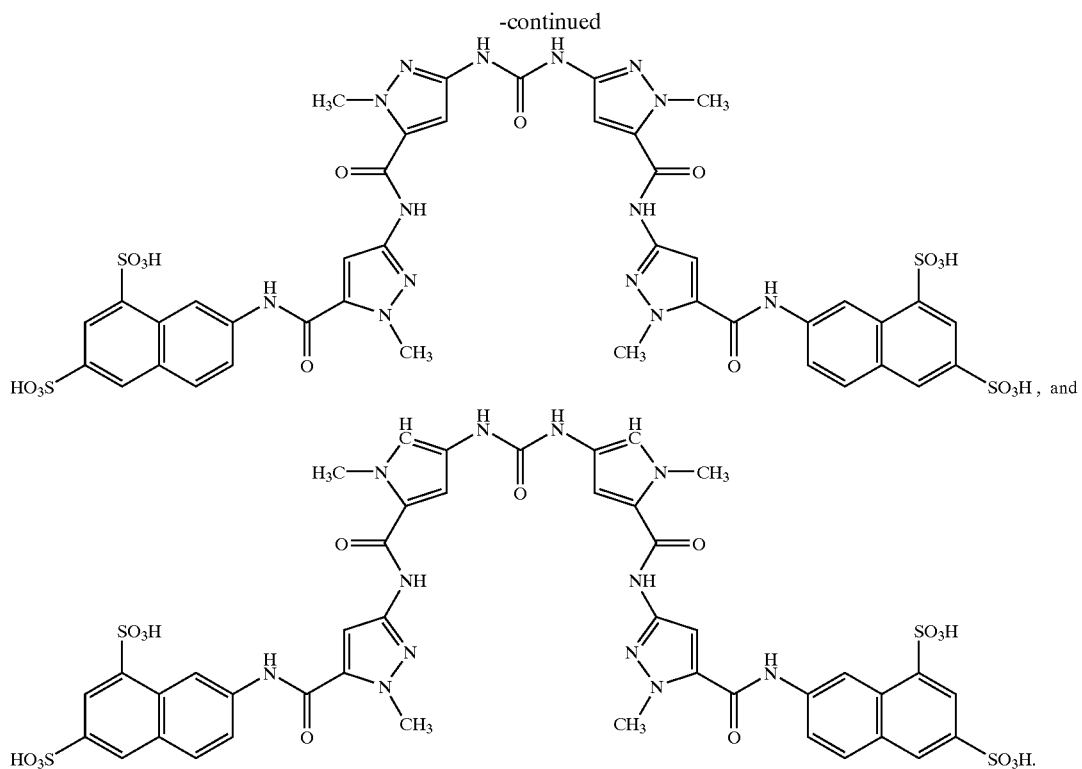

These compounds are also known in the art by the NSC Nos. 645793, 645794, 651015, 651016, 651017, 658434, 662162, 668535, 668536, and 668537, respectively. Additionally, the value of m and n in these compounds is two. Other well-known compounds of formula I, wherein m and n are larger (e.g., 3) or smaller (e.g., 1), include 664740, 664739, 670886, 670887, and 670888 (see Clanton et al., supra).

The compounds of the present invention, and the salts thereof, can be prepared by a process comprising reacting a compound of formula (II):

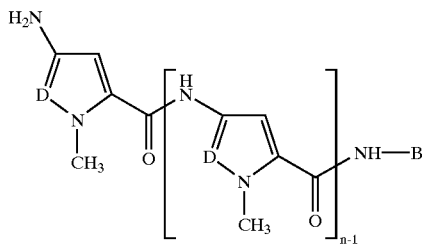

wherein n and B are as defined above with respect to formula (I), or a salt thereof, with a compound of formula (III):

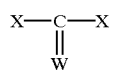

wherein W is as defined above with respect to formula (I), and each of the X groups, which can be the same or different, is a good leaving group. As is well known in the art, suitable salts of formula (I) can be obtained, as well as the corresponding free acid of formula (I). A salt of a compound of formula (II) can be a salt with inorganic bases, for example those mentioned above with respect to pharmaceutically acceptable salts. Sodium and potassium salts are among the preferred salts of the invention. Preferred examples of good leaving groups, denoted as X in formula (III), are halogen atoms, in particular chlorine, or other easily displaceable groups, such as imidazolyl, triazolyl, p-nitrophenoxy and trichlorophenoxy.

The reaction of a compound of formula (II), or a salt thereof, with a compound of formula (III) can be carried out according to well-known methods. When X is a halogen atom, the reaction is preferably carried out at a molar ratio of compound (II):compound (III) from about 1:1 to about 1:4. The reaction can be performed in organic solvents, such as dimethylsulfoxide, hexamethylphosphotriamide, dimethylacetamide or, preferably, dimethylformamide, or their aqueous mixtures, or in water/dioxane or water/toluene mixtures, in the presence of either an organic base (e.g., triethylamine or diisopropylethylamine), or an inorganic base (e.g., sodium bicarbonate or sodium acetate). The reaction temperature can vary from about −10° C. to about 50° C. with a reaction time from about 1 hr to about 12 hrs.

The compounds of formula (I) prepared according to the above-described procedures can be purified by any suitable technique. Such techniques include conventional methods, such as silica gel or alumina column chromatography, and/or by re-crystallization from organic solvents (e.g., lower aliphatic alcohols or dimethylformamide).

The compounds of formula (II) can be obtained according to known procedures. For instance, a compound of formula (II) can be obtained by reduction of a compound of formula (IV):

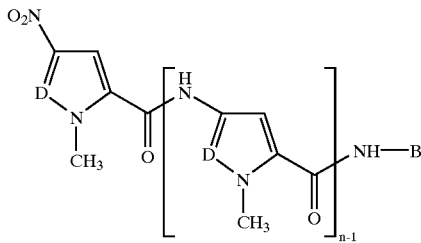

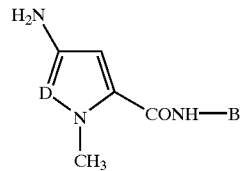

wherein n and B are as defined above, by methods wellknown in the art. For example, the compounds of formula (IV) can be obtained by reacting an amine of formula B—NH$_2$, wherein B is defined as above with respect to formula (I), with a compound of formula (V):

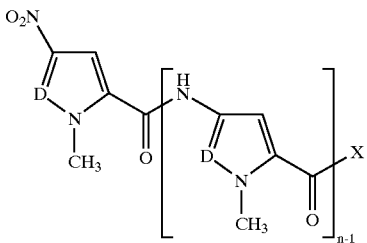

wherein n and X are as defined above with respect to formula (I).

The reaction of an amine of formula B—NH$_2$ with a compound of formula (V) is also a well-known process. Alternatively, a compound of formula (IV), wherein n is 2 or more, can be obtained by a multi-step-process comprising reacting a compound of formula (VI):

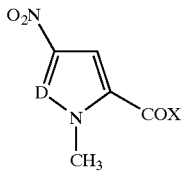

wherein X is as defined above with respect to formula I, with an amine of formula B—NH$_2$, in which B is as defined above with respect to formula (I). The reaction, which can be carried out according to known methods, provides compounds of formula (VII):

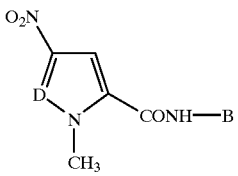

wherein B is as defined above with respect to formula (I).

A compound of formula (VII) is reduced according to known methods to provide a compound of formula (VIII):

wherein B is as defined above with respect to formula (I), which in its turn is reacted with a compound of formula (VI), thus obtaining a compound of formula (IV), wherein n is 2. If a compound of formula (IV), wherein n is 3 or more is desired, a further reduction and acylation step is performed.

The compounds of formula (V) are known compounds and can be obtained, for example, according to *Heterocycles*, 27, 1945–1952 (1988).

The compounds of formula (VI) and the amine of formula B—NH$_2$ are known products and can be easily obtained according to known methods.

The compounds useful in the context of the present inventive method can be administered to an animal, especially a mammal (e.g., a mouse), and preferably a human, by any suitable means or routes. Such administration means or routes include, but are not limited to, intraperitoneally, subcutaneously, and intravenously. The compounds of the present invention should not ordinarily be administered orally, unless the inflammation occurs in the gastrointestinal tract, especially, before the stomach.

The dosage depends on the age, weight and condition of the patient and on the administration route. For example, a suitable dosage for systemic administration to adult humans in reasonably good health can range from about 0.5 to about 1000 mg per dose 1–4 times a day. For local administration (e.g., subcutaneously or topically), the compound should be present in a suitable concentration. For example, a solution of about 0.0001% to about 2.5% (weight/volume) of a compound of formula I can be injected at a site of local inflammation. Further, one skilled in the art will understand how to vary the dosage according to the particular needs of the patient based on the particular pharmacokinetics of the animal to be treated. For example, in the mouse, following intravenous administration of 50 mg/kg body weight, a peak concentration of about 700 $\mu$M NSC 651016 is obtained. This concentration decreases with a half-life of about 50 hrs so that >10 $\mu$M NSC 651016 remains in the circulation for over 24 hrs.

Pharmaceutical compositions useful in the context of the invention can comprise a compound of formula (I) as the active substance, in association with one or more pharmaceutically acceptable excipients and/or carriers. The pharmaceutical compositions of the invention are usually prepared following conventional methods and are administered in a pharmaceutically suitable form.

For instance, solutions for intravenous injection or infusion can contain as carrier, for example, sterile water or sterile aqueous isotonic saline solutions. Suspensions or solutions for intramuscular injections can contain, together with the active compound, a pharmaceutically acceptable carrier, e.g., sterile water, olive oil, ethyl oleate, glycols, e.g., propylene glycol, and, if desired, a suitable amount of lidocaine hydrochloride. In the forms for topical application, e.g., creams, lotions, or pastes for use in dermatological treatment, the active ingredient can be mixed with conventional oleaginous or emulsifying excipients.

While the method of the present invention is useful in the inhibition of inflammation in general, it is particularly useful in the inhibition of non-TNF-α-dependent inflammation. Non-TNF-α-dependent inflammation can be caused by any one of a number of conditions or disease states, such as asthma, allergy, blunt-force trauma, reperfusion injury, non-bacteria-mediated respiratory distress syndrome, and other conditions, such as the demyelination of nerve tissue, such as that which is associated with multiple sclerosis.

The method of inhibiting non-TNF-α dependent inflammationis particularly useful for inhibiting inflammation that is mediated through a chemokine. A review of the disease states associated with particular populations of chemokines, is found in Howard et al., *Trends in Biotech.*, 14, 46–51 (1996). Furthermore, due to the known capacity of chemokines to activate selectively and control the movement of a specific population(s) of inflammatory cells, one with ordinary skill in the art can determine other inflammatory conditions that can be inhibited in accordance with the present inventive method by determining the population of inflammatory cells at the site of inflammation (e.g., by performing such assays as a blister test, an ELISA for fluid aspirates, or a biopsy for solid tumors). Alternatively, one with ordinary skill in the art can determine inflammatory conditions that can be inhibited in accordance with the present inventive method by determining which chemokines are present at the site of inflammation. Since many of the chemokine and chemokine receptor genes have been cloned and there are also monoclonal antibodies directed to many of the chemokines, one skilled in the art could perform Southern Blot, in situ hybridization, Western Blots or ELISA analysis to determine which chemokines are present in the inflamed tissue. Alternatively, the infiltrate in inflamed tissue can be examined, such as in accordance with the methods set forth in Examples 14 and 15.

The non-TNF-α dependent inflammation can be mediated through an α-chemokine, such as SDF-1α. Alternatively, the non-TNF-α-dependent inflammation can be mediated through a β-chemmokine, such as MIP-1α, HCC-1, LEC, TARC, Eotaxin, or RANTES. The chemokine that mediates the non-TNF-α-dependent inflammation can be encoded by a virus and can be determined in accordance with methods known in the art. If encoded by a virus, preferably the chemokine is encoded by a herpesvirus, such as CMV, *Herpes saimiri*, HHV8 or HHV6.

Also, in the method of inhibiting non-TNF-α-dependent inflammation, the inflammation can be mediated through a chemokine receptor. The chemokine receptor can be an α-chemokine receptor, such as CXCR4. The chemokine receptor alternatively can be a β-chemmokine receptor, such as CCR1, CCR3, CCR5, and CCR8. Further, the α- or β-chemokine receptor can be encoded by a virus. The virally encoded α- or βchemokine receptor is preferably encoded by a herpesvirus, such as CMV, *Herpes saimiri*, HHV8 or HHV6.

EXAMPLES

The following examples illustrate but do not limit the invention.

Example 1

8,8'-(Carbonyl-bis(imino-N-methyl-4,2-pyrrolecarbonyl-imino(N-methyl-4,2-pyrrole)carbonylimino))bis(1,5-naphthalendisulfonic Acid) tetrasodium Salt To a solution of 8-(amino-N-methyl-4,2-pyrrolecarbonyl-imino(N-methyl-4,2-pyrrole)carbonylmino))(1,5-naphthalendisulfonic acid) disodium salt hydrochloride (0.6 g., $1.0210^3$ mol) in water (20 ml), sodium acetate (0.328 g., 4 mmols) was added with stirring. The whole reaction was cooled to 0° C. with an ice-salt bath, then a solution of phosgenein toluene (1 ml, about 4 eq.) was added dropwise. The mixture was stirred for 1 hr. at 0° C.

The solvents were evaporated under vacuum and the residue was taken up with methanol and filtered. The filtrate was evaporated and the residue was chromatographed on a silica gel column with methylene chloride:methanol 60:40 as eluent, affording 0.16 g of the title compound.

I.R. (KBr) cm$^{-1}$: 3440 b, 1660, 1640, 1585, 1180, 1030. N.M.R. (DMSO-d6): δ 3.84 (3H, s); 3.85 (3H, s); 6.80 (1H, d); 7.07 (2H, m); 7.41 (2H, m); 7.92 (2H, dd); 8.12 (1H, s); 8.27 (1H, dd); 9.07 (1H, dd); 9.90 (1H, bs); 12.27 (1H, bs). F.A.B.-M.S.: m/z 1209; M++1; 1231, M++23; 1128, M-80 U.V. (H$_2$O) nm: λ max (E$_{1\ cm}$ 1%): 316 (331), 229 (478).

The following compounds are obtained by analogous procedure:

8,8'-(carbonyl-bis(imino-N-methyl-4,2-pyrrole-carbony-imino(N-methyl-4,2-pyrrole)carbonylimino))bis(3-naphthalensulfonic acid)disodium salt. I.R. (KBr) cm$^{-1}$: 3430 b, 1640, 1585, 1200, 1030. N.M.R. (DMSO-d6): δ 3.84 (6H, s); 6.86 (1H, d); 7.05 (1H, d); 7.24 (1H, d); 7.35 (1H, d); 7.54 (2H, m); 7.70 (1H, dd); 7.90 (2H, m); 8.15 (1H, d); 8.15 (1H, d); 8.95 (1H, bs); 9.94 (1H, bs); 10.03 (1H, bs). F.A.B. M.S.: m/z 1005, M++H; 1027, M++Na. U.V. (H$_2$O)nm: λ max (E$_{1\ cm}$ 1%): 304 (366), 226 (1002);

8,8'-(carbonyl-bis(imino-N-methyl-4,2-pyrrolecarbonyl-amino(N-methyl-4,2-pyrrole)carbonylimino))bis(1-naphthalensulfonic acid) disodium salt;

8-8'-(carbonyl-bis(imino-N-methyl-4,2-pyrrolecarbonyl-imino(N-methyl-4,2-pyrrole)carbonylimino))bis(5-naphthalensulfonic acid) disodium salt;

8,8'-(carbonyl-bis(imino-N-methyl-4,2-pyrrolecarbonyl-imino(N-methyl-4,2-pyrrole)carbonylimino))bis(1,3-naphthalendisulfonic acid) tetrasodium salt;

8-8'-(carbonyl-bis(imino-N-methyl-4,2-pyrrolecarbonyl-imino(N-methyl-4,2-pyrrole)carbonylimino))bis(3,5-naphthalendisulfonic acid) tetrasodium salt;

8,8'-(carbonyl-bis(imino-N-methyl-4,2-pyrrolecarbonyl-imino(N-methyl-4,2-pyrrole)carbonylimino))bis(2,5-naphthalendisulfonic acid) tetrasodium salt;

8,8'-(carbonyl-bis(imino-N-methyl-4,2-pyrrolecarbonyl-imino(N-methyl-4,2-pyrrole)carbonylimino))bis(2,4-naphthalendisulfonic acid) tetrasodium salt;

8-8'-(carbonyl-bis(imino-N-methyl-4,2-pyrrolecarbonyl-imino(N-methyl-4,2-pyrrole)carbonylimino))bis(1,6-naphthalendisulfonic acid) tetrasodium salt;

8,8'-(carbonyl-bis(imino-N-methyl-4,2-pyrrolecarbonyl-imino(N-methyl-4,2-pyrrole)carbonylimino))bis(2,6-naphthalendisulfonic acid) tetrasodium salt; and 8-8'-(carbonyl-bis(imino-N-methyl-4,2-pyrrolecarbonyl-imino(N-methyl-4,2-pyrrole)carbonylimino))bis(3,6-naphthalendisulfonic acid) tetrasodium salt.

Example 2

8,8'-(Carbonyl-bis(imino-N-methyl-4,2-pyrrolecarbonyl-imino(N-methyl-4,2-pyrrole)carbonylimino))bis(1,3,5-naphthalentrisulfonic Acid)hexasodium Salt To a solution of 8-(amino-N-methyl-4,2-pyrrolecarbonyl-imino(N-methyl-4,2-pyrrole)carbonylimino))(1,3,5- naphthalentrisulfonic acid trisodium salt)hydrochloride (2.19 g, 3 mmols) in water (60 ml) and dioxane (15 ml), sodium acetate (0.984 g, 12 mmols) was added under stirring. The whole was cooled to 8° C. with an ice bath, then a 20% solution of phosgene in toluene (3 ml, 6 mmols), diluted with 9 ml of dioxane, was added dropwise in 1 hr. The mixture was stirred 2 hr. at 8° C. The solvents were evaporated under vacuum and the residue was taken up with methanol. After filtration of the salts, the filtrate was evaporated and the residue was cromotographed on a silica gel column with methylene chloride:methanol:water 60:40:4 as eluent, affording 0.82 g of the title compound.

I.R. (KBr)cm$^{-1}$: 3440 b, 1640, 1590, 1190, 1030. N.M.R. (DMSO-d6): δ 3.80 (3H, s); 3.83 (3H, s); 6.80 (1H, d); 7.06 (2H, m); 7.40 (1H, d); 7.88 (1H, d); 7.99 (1H, d); 8.02 (1H, bs); 8.57 (1H, d); 9.33 (1H, d); 9.91 (1H, bs); 12.29 (1H, bs). F.A.B.-M.S: m/z 1411, M$^-$–H; 1389, M$^-$–Na. U.V. (H$_2$O) nm: λ max (E$_{1\ cm}$ 1%): 311 (266), 233 (551).

The following compounds can be obtained by analogous procedure:

8-8'-(carbonyl-bis(imino-N-methyl-4,2-pyrrolecarbonyl-imino(N-methyl-4,2-pyrrole)carbonylimino))bis(1,4,6-naphthalentrisulonic acid) hexasodium salt;

8,8'-(carbonyl-bis(imino-N-methyl-4,2-pyrrolecarbonyl-imino(N-methyl-4,2-pyrrole)carbonylimino))bis(2,4,6-naphthalentrisulfonic acid) hexasodium salt;

8,8'-(carbonyl-bis(imino-N-methyl-4,2-pyrrolecarbonyl-imino(N-methyl-4,2-pyrrole)carbonylimino))bis(1,3,6-naphthalentrisulfonic acid) hexasodium salt; and 8,8'-(carbonyl-bis(imino-N-methyl-4,2-pyrrolecarbonyl-imino(N-methyl-4,2-pyrrole)carbonylimino))bis(2,3,5-naphthalentrisulfonic acid) hexasodium salt.

Example 3

8-(Amino-N-methyl-4,2-pyrrolecarbonyl-imino(N-methyl-4,2-pyrrole)carbonylimino))(1,3,5-naphthalentrisulfonic Acid Trisodium Salt) hydrochloride The compound 8-(nitro-N-methyl-4,2-pyrrolecarbonyl-imino(N-methyl-4,2-pyrrole)carbonylimino))(1,3,5-naphthalentrisulfonic acid trisodium salt) (2.17 g; 3 mmol) was dissolved into a mixture of water (120 ml) and 1 N HCl (3 ml) and reduced over a Pd catalyst (10% on carbon; 900 mg) under H$_2$ pressure (50 p.s.i.) for 3 hours. The catalyst was filtered and the resulting solution was concentrated in vacuum to dryness, affording 2.1 g of the title compound.

I.R. (KBr) cm$^{-1}$: 3440 b, 1640, 1520, 1190, 1030. N.M.R. (DMSO-d6): δ 3.85 (3H, s); 3.90 (3H, s); 7.1 (3H, m); 7.4 (1H, d); 7.95 (2H, m); 8.60 (1H, d); 9.35 (1H, d); 10.1 (4H, bs); 12.3 (1H, bs).

Example 4

8-(Nitro-N-methyl-4,2-pyrrolecarbonyl-imino(N-methyl-4,2-pyrrole)carbonylimino))(1,3,5-naphthalenetrisulfonic Acic Trisodium Salt)

To a solution of 8-(amino(N-methyl-4,2-pyrrole) carbonylimino)(1,3,5-naphthalentrisulfonic acid trisodium salt)hydrochloride (1.824 g, 3 mmol) in water (45 ml) and 1N NaOH (1 ml), sodium acetate (0.492 g, 6 mmol) was added under stirring. The solution was cooled to 5° C. with an ice bath, then a solution of (4-nitro-N methyl-2-pyrrole) carbonyl chloride (0.567 g, 3 mmol) in dioxane (30 ml) was added dropwise in 1 hr. The mixture was stirred 1 hr at 5° C., acidified to pH 4 with 1 N HCl and evaporated under vacuum to dryness. The residue was treated with ethyl acetate (300 ml), stirred for 1 hr. and filtered, to obtain 2.1 g of the title compound.

I.R. (KBr) cm$^{-1}$ 3440 b, 1650, 1520, 1305, 1195, 1030. N.M.R. (DMSO-d6; 80 M.Hz.) δ:3.89 (3H, s); 3.99 (3H, s); 7.18 (1H, d); 7.46 (1H, d); 7.70 (1H, d); 8.02 (2H, m); 8.2 (1H, d); 8.63 (1H, d); 9.41 (1H, d); 10.45 (1H, b s); 12.42 (1H, b s).

Example 5

8-(Amino(N-methyl-4,2-pyrrole)carbonylimino)(1,3,5-naphthalentrisulfonic Acid Trisodium Salt), Hydrochloride The solution of 8-(nitro(N methyl-4,2-pyrrole) carbonylimino) (1,3,5-naphthalentrisulfonic acid trisodium salt) (1.803 g; 3 mmol) in water (120 ml) and 1 N HCl (3 ml) was reduced over a Pd catalyst (10% on 800 g carbon) under H$_2$ pressure (50 p.s.i.) for 4 hr. The catalyst was filtered and the resulting solution was concentrated in vacuum to dryness, affording 1.8 g of the title compound.

I.R. (KBr) cm$^1$: 3440 b, 1640, 1520, 1190, 1030. N.M.R. (DMSO-d6): δ 3.9 (3H, s); 7.11 (1H, d); 7.29 (1H, d); 8.04 (2H, m); 8.6 (1H, d); 9.88 (1H, d); 10.04 (3H, b s); 12.39 (1H, b s).

Example 6

8-(Nitro(N-methyl-4,2-pyrrole)carbonylimino)(1,3,5-naphthalentrisulfonic Acid Trisodium Salt)

To a solution of 8-amino, 1,3,5-naphthalentrisulfonic acid trisodium salt (1.347 g, 3 mmol) in water (45 ml), sodium acetate (0.492 g) was added under stirring. The solution was cooled to 5° C. with an ice bath, then a solution of (4-nitro-N methyl-2-pyrrole)carbonyl chloride (0.943, 5 mmol) in dioxane (45 ml) was added dropwise in 1 hr. The mixture was stirred for 3 hr at 5° C., acidified to pH 4 with 1 N HCl and evaporated under vacuum to dryness. The residue was treated with ethylacetate (300 ml), stirred for 1 hr., and filtered to obtain 1.7 g of the title compound.

I.R. (KBr) cm$^1$: 3440 b, 1650, 1530, 1305, 1200, 1030. N.M.R. (DMSO-d6): δ 3.96 (3H, s); 7.84 (1H, d); 8.06 (2H, m); 8.15 (1H, d); 8.63 (1H, d); 9.4 (1H, d); 12.55 (1H, bs).

Example 7

7,7'-(Carbonyl-bis(imino-N-methyl-4,2-pyrrole) carbonylimino))(N-methyl-4,2-pyrrole) carbonylimino))bis(1,3-naphthalendisulfonic Acid) tetrapotassium Salt To a solution of 7-(amino-N-methyl-4,2-pyrrolecarbonylimino(N-methyl-4,2-pyrrole) carbonylimino))(1,3-naphthalendisulfonic acid dipotassium salt) hydrochloride (160 mg, 0.24 mmol) in water (15 ml) and dioxane (10 ml), potassium acetate (50 mg, 0.51 mmol) was added under stirring. A 20% solution of phosgene in toluene (0.5 ml, 1 mmol), diluted with dioxane (2 ml), was added dropwise in 30 minutes at room temperature. The mixture was stirred 1 hr. at room temperature. The solvents were evaporated under vacuum, and the residue was cromatographed on a silica gel column with methylene chloride:methanol:water 40:60:6 as eluent, affording 90 mg of the title compound.

I.R. (KBr) cm$^{-1}$: 3450 (b); 1650; 1580; 1530; 1190; 1030. N.M.R. (DMSO-d6): δ 3.84 (3H, s); 3.87 (3H, s); 6.80 (1H, d); 7.05 (1H, d); 7.18 (1H, d); 7.33 (1H, d); 7.86 (2H, m); 8.00 (1H, d); 8.16 (1H, bs); 8.21 (1H, d); 8.95 (1H, bs); 9.86 (1H, bs); 10.21 (1H, bs). U.V. ($H_2O$)mm: λ max ($E_1$ cm 1%): 316.8 (371), 248.95 (444). F.A.B. M.J.: m/z: 1273 (M++H); 1311 (M++K).

The following compounds which can be obtained by analogous procedure:

7,7'-(carbonyl-bis(imino-N-methyl-4,2-pyrrolecarbonyl-imino(N-methyl-4,2-pyrrole)carbonylimino))bis(1-naphthalensulfonic acid) disodium salt;

7,7'-(carbonyl-bis(imino-N-methyl-4,2-pyrrolecarbonyl-imino(N-methyl-4,2-pyrrole)carbonylimino))bis(2-naphthalensulfonic acid) disodium salt;

7,7'-(carbonyl-bis(imino-N-methyl-4,2-pyrrole-carbonyl-imino(N-methyl-4,2-pyrrole)carbonylimino))bis(3-naphthalensulfonic acid) disodium salt;

7,7'-(carbonyl-bis(imino-N-methyl-4,2-pyrrolecarbonyl-imino(-methyl-4,2-pyrrole)carbonylimino))bis(4-naphthalensulfonic acid) disodium salt;

7,7'-(carbonyl-bis(imino-N-methyl-4,2-pyrrolecarbonyl-imino(N-methyl-4,2-pyrrole)carbonylimino))bis(2,3-naphthalendisulfonic acid) tetrasodium salt;

7,7'-(carbonyl-bis(imino-N-methyl-4,2-pyrrolecarbonyl-imino(N-methyl-4,2-pyrrole)carbonylimino))bis(2,4-naphthalendisulfonic acid) tetrasodium salt;

7,7'-(carbonyl-bis(imino-N-methyl-4,2-pyrrolecarbonyl-imino(N-methyl-4,2-pyrrole)carbonylimino))bis(1,5-naphthalendisulfonic acid) tetrasodium salt;

7,7'-(carbonyl-bis(imino-N-methyl-4,2-pyrrolecarbonyl-imino(N-methyl-4,2-pyrrole)carbonylimino))bis(2,5-naphthalendisulfonic acid) tetrasodium salt;

7,7'-(carbonyl-bis(imino-N-methyl-4,2-pyrrolecarbony-imino(N-methyl-4,2-pyrrole)carbonylimino))bis(3,5-naphthalendisulfonic salt;

7,7'-(carbonyl-bis(imino-N-methyl-4,2-pyrrolecarbonyl-imino(N-methyl-4,2-pyrrole)carbonylimino))bis(1,6-naphthalendisulfonic acid) tetrasodium salt;

7,7'-(carbonyl-bis(imino-N-methyl-4,2-pyrrlecarbonyl-imino(N-methyl-4,2-pyrrole)carbonylimino))bis(2,6-naphthamendisulfonic acid) tetrasodium salt;

7,7-(carbonyl-bis(imino-N-methyl-4,2-pyrrolecarbonyl-imino(N-methyl-4,2-pyrrole)carbonylimino))bis(3,6-naphthalendisulfonic acid) tetrasodium salt;

7-7'-(carbonyl-bis(imino-N-methyl-4,2-pyrrolecarbonyl-imino(N-methyl-4,2-pyrrole)carbonylimino))bis(1,3,5-naphthalentrisulfonic acid) hexasodium salt;

7,7'-(carbonyl-bis(imino-N-methyl-4,2-pyrrolecarbonyl-imino(N-methyl-4,2-pyrrole)carbonylimino))bis(1,4,6-naphthalentrisulfonic acid) hexasodium salt;

7,7'-(carbonyl-bis(imino-N-methyl-4,2-pyrrolecarbonyl-imino(N-methyl-4,2-pyrrole)carbonylimino))bis(1,3,6-naphthalentrisulfonic acid) hexasodium salt;

7,7'-(carbonyl-bis(imino-N-methyl-4,2-pyrrole-carbonyl-imino(N-methyl-4,2-pyrrole)carbonylimino))bis(2,4,6-naphthalentrisulfonic acid) hexasodium salt;

7,7'-(carbonyl-bis(imino-N-methyl-4,2-pyrrolecarbonyl-imino(N-methyl-4,21-pyrrole)carbonylimino))bis(2,3,5-naphthalentrisulfonic acid) hexasodium salt;

2,2'-(carbonyl-bis(imino-N-methyl-4,2-pyrrolecarbonyl-imino(N-methyl-4,2-pyrrole)carbonylimino))bis(2-deoxy-D-glucose-6-sulfate) disodium salt;

2,2'-(carbonyl-bis(imino-N-methyl-4,2-pyrrolecarbonyl-imino(N-methyl-4,2-pyrrole)carbonylimino))bis(2-deoxy-D-glucose-6-phosphate) disodium salt;

5,5'-(carbonyl-bis(imino-N-methyl-4,2-pyrrocarbonyl-imino(N-methyl-4,2-pyrrole)carbonylimino))bis(8-quinolinesulfonic acid) disodium salt;

5,5'-(carbonyl-bis(imino-N-methyl-4,2-pyrrolecarbonyl-imino(N-methyl-4,2-pyrrole)carbonylimino))bis(6-quinolinesulfonic acid) disodium salt;

8,8'-(carbonyl-bis(imino-N-methyl-4,2-pyrrolcarbonyl-imino(N-methyl-4,2-pyrrole)carbonylimino))bis(5,7-quinolinedisulfonic acid) tetrasodium salt; and 5,5'-(carbonyl-bis(imino-N-methyl-4,2-pyrrolecarbonyl-imino(N-methyl-4,2-pyrrole)carbonylimino))bis(6,8s-quinolinedisulfonic acid) tetrasodium salt.

Example 8

8,8'-Carbonyl-bis(imino-N-methyl-4,2-pyrrolecarbonyl-imino(N-methyl-4,2-pyrrole) carbonylimino))bis(1,3,5-naphthanentrisulfonic Acid)

A solution of 8,8'-(carbonyl-bis(imino-N-methyl-4,2-pyrrolecarbonyl-imino(N-methyl-4,2-pyrrole) carbonylimino))bis(1,3,5-naphthalentrisulfonic acid) hexasodium salt (400 mg) in water (10 ml) is chromatographed on an Amberlite 1R-120(H) column (20 ml), with water as eluent. The solution is evaporated to dryness in vacuum, affording 0.3 g of the title compound.

Example 9

The following example demonstrates the ability of a compound of formula I, NSC 651016, to inhibit the binding of both α- and β-chemokines to cells expressing receptors for the same. This example also demonstrates that monomeric distamycin derivatives do not block the binding of these cytokines to their respective receptors.

HEK-293 cells (293 cells) do not express β-chemmokine receptors. The 293 cells were, therefore, transfected with gene transfer vectors encoding for CCR5, a β-chemokine receptor, which allows the transfected cells to bind such β-chemmokinesas RANTES, MIP1α, and MIP1β. Radiolabeled RANTES, MIP1α, and MIP1β (0.2 ng) were individually added to tubes containing increasing concentrations of unlabeled NSC 651016. The 293 cells ($1\times10^6$ cells/ml) were then added to the individual tubes and mixed by continuous rotation at room temperature for 45 minutes. After incubation, the cells were centrifuged through a 10% sucrose/PBS cushion and the cell-associated radioactivity was measured using a 1272 Wallace gamma counter. The inhibition of chemokine binding increased with increasing concentrations of the NSC 651016 compound. In the presence of the highest tested dose (200 μM NSC 651016), the binding of RANTES, MIP1α, and MIP1β was inhibited by about 65%, 37%, and 20%, respectively. In contrast, the monomeric form of 651016, i.e.,

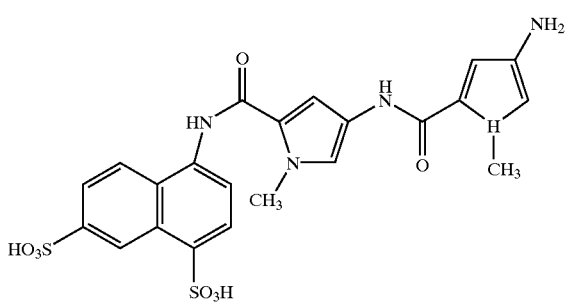

and 645795 inhibited chemokine binding by about 0 to 10% in each measured instance (also at 200 µM). Similarly, when 293 cells were transfected with an expression vector for CXCR4, an α-chemokine receptor, the binding of SDF-1α (an α-chemokine ligand) was inhibited by about 88% by administration of 200 µM 651016 and by about 40% by 75 µM 651016. The inhibition of chemokine binding to CCR1 and CCR3 was also observed in similarly performed assays. In contrast, IL-8 binding to 293 cells transfected with the CXCR2 receptor was not inhibited by any of the compounds tested, which indicates that the active compounds of the inventive method mediate their inhibitory activity through particular chemokine receptors and do not act through nonspecific toxicity.

Example 10

This example demonstrates that the interaction of selected chemokines with a population of normal leukocytes, such as monocytes, can be inhibited by the method of the present invention. Accordingly, normal monocytes can be inhibited from migrating to sites of inflammation.

In contrast to the HEK-293 cells, which do not express chemokine receptors, normal human monocytes express a variety of chemokine receptors, including the CXCR4 and CCR5 receptors which bind the α-chemokine SDF-1α and the β-chemokines RANTES, MIP1α and MIP1β. Using the method described in Example 9, radiolabeled SDF-1α and RANTES were added to increasing concentrations of unlabeled NSC 651016 and incubated with normal human monocytes ($4 \times 10^6$ cells) at room temperature for two hours. Measuring the cell-associated radioactivity revealed that NSC 651016 (200 µM) inhibited the binding of SDF-1α, RANTES, MIP-α, and MIP-β to human peripheral blood monocytes by 88%, 68%, 75%, and 31%, respectively. Since these chemokines are associated with leukocyte chemotaxis to sites of inflammation, this example demonstrates that, by interfering with the ligand-receptor interaction, the NSC 651016 compound can inhibit normal monocytes from migrating to sites of inflammation.

Example 11

This example provides evidence that a compound of formula 1, NSC 651016, can block the chemokine ligand-receptor interaction.

Competition assays were performed with the 44716.111 mouse monoclonal antibody (mAb), which binds to the extracellular domain of the CXCR4 chemokine receptor. Human monocytes, which express the CXCR4 chemokine receptor, were pre-incubated with either 125 nM of SDF-1α or 200 µM NSC 651016 for 15 min at 4° C. Control monocyte cells were placed at 4° C. for 15 min. The cells were then incubated with the 44716.111 mAb for an additional 30 min. The presence of the 44716.111 mAb was detected by incubating the cells with FITC-conjugated anti-murine antibody and subjecting the cells to FACS Analysis. As expected, treatment with the SDF-1α chemokine resulted in a decrease in 44716.111 antibody binding to the CXCR4 receptor, due to SDF-1α ligand binding to the CXCR4 receptor. Treatment with the NSC 651016 compound resulted in the same decrease in 44716.111 antibody binding, indicating that the NSC 651016 compound specifically interacts with the CXCR4 receptor and can block subsequent chemokine binding.

Example 12

This example demonstrates the ability of a compound of formula 1, NSC 651016, to block the intracellular calcium flux that is induced by α- and β-chemmokine. Intracellular calcium flux in response to chemokines is believed to be involved in intracellular signaling that contributes to leukocyte chemotaxis.

Using the standard techniques disclosed by Badolato et al., J. Immuno., 155, 4004 (1995), it was demonstrated that the compounds useful in the context of the present invention do not themselves induce intracellular calcium flux. Furthermore, 200 µM of NSC 651016 completely blocked the intracellular calcium flux induced by MIP1α in normal peripheral blood monocytes. The concentration at which 50% of the MIP-1α induced calcium flux was blocked was 5 µM NSC 651016. In addition to MIP-1α, the RANTES, MIP-1β, and SDF-1α chemokine-induced intracellular calcium flux was blocked by NSC 651016. Importantly, cells treated with 200 µM NSC 651016 and fMLP, a chemoattractant that does not bind to chemokine receptors, demonstrated a physiologically appropriate calcium influx. This shows that NSC 651016 and the other compounds useful in the context of the present inventive method selectively affect chemokine signaling without non-specific toxicity.

Example 13

This example demonstrates the ability of NSC 651016 to block chemotaxis by murine spleen cells in vitro. The ability of particular compounds useful in the context of the present invention to block the chemotaxis of spleen cells is indicative of their utility to inhibit both TNF-α-dependent and non-TNF-α dependent inflammation.

Murine spleen cells were "panned" on plastic to remove the adherent cells. The recovered cells were incubated for 30 minutes at 37° C. with one of the following: NSC 651015, NSC 651016, NSC 662162, and NSC 680651. The cells exhibited a chemotactic index of 1 when incubated in media alone, 2.3 when incubated in 10 ng/ml RANTES, and from about 1 to about 1.5 when incubated with RANTES and either a $10^{-6}$M or a $10^{-11}$ M concentration of the compounds of formula (I). This assay demonstrates the ability of formula I compounds to inhibit β-chemokine mediated chemotaxis of splenocyte cells. In assays similarly performed using either the MIP-1α or the SDF-1α chemokine rather than RANTES, chemotactic inhibition was also observed in the presence of formula I compounds. However, cells treated with the formula I compound NSC 651016 did not inhibit MCP-1 induced chemotaxis, demonstrating that NSC 651016 action is not indiscriminate.

Therefore, each of the compounds useful in the context of the present invention tested in this assay shows the ability to inhibit selectively the chemotaxis of non-adherent splenocytes. Non-adherent splenocytes are predominantly lymphocytes that home to sites of injury in vivo, which is partially and substantially responsible for inflammation. The ability of the compounds tested to block this inflammation indicates that these compounds can inhibit inflammation, irrespective of the role of TNF-α in the inflammation.

Example 14

This example demonstrates the ability of a compound of formula I, NSC 651016, to decrease inflammation in a murine model system.

One microgram of RANTES in PBS was administered simultaneously to a balb/c mouse with or without 1 μg of NSC 651016 in PBS. Forty-eight hours later, the site of injection was scored for infiltration of polymorphic nuclear cells (neutrophils) and mononuclear cells (i.e., the remaining leukocytes). The level of inflammation was scored using a four point scale, wherein a score of 1 indicated few infiltrating cells and a score of 4 indicated many infiltrating cells. Three tests were performed. When RANTES was administered alone, the pathologist scored the three tests of infiltration by neutrophils as 1, 2, 2 (i.e., 2) and the infiltration by mononuclear cells as 2, 2, 2 (i.e., 2). When NSC 651016 was simultaneously administered with the RANTES, the pathologist scored the infiltration in all tests as 1. Thus, NSC 651016 inhibited the infiltration of leukocytes in vivo in response to RANTES, which is a chemokine that functions independently of TNF-α. Since infiltration of leukocytes into a tissue in response to chemokines is a hallmark of inflammation, this example demonstrates a routine assay by which these compounds useful in the context of the present inventive method can be shown to possess anti-inflammatory activity.

Example 15

This example demonstrates the ability of a compound of formula I, NSC 651016, to decrease inflammation in an in vivo human-murine model system, using CB17 SCID mice. CB17 SCID mice, which have no typical T lymphocytes in their immune system, are useful in vivo model systems because they are tolerant of human T lymphocytes.

CB17 SCID mice (25 g) were injected with $10^8$ human plasma blood leukocytes (PBLs) at time 0. RANTES (1 μg) and NSC 651016 (100 μg) were co-injected at 0, 24 and 48 hrs. Immunohistology of the injection site was performed at 72 hrs to determine the inflammatory response, which was measured by determining the level of infiltration of lymphocytes to the injection site in response to the RANTES chemokine. When RANTES was administered alone, the three tests of infiltration by T lymphocytes were scored as 2,2,3 using a four point scale like that described in Example 14 with respect to neutrophils. When NSC 651016 was simultaneously administered with the RANTES, the infiltration in all tests was scored as 1, indicating that NSC 651016 inhibited the infiltration of lymphocytes in vivo in response to RANTES.

All references cited herein (e.g., Clanton et al. (1995), supra) are hereby incorporated by reference to the same extent as if each reference were individually and specifically indicated to be incorporated by reference and were set forth in its entirety herein.

While this invention has been described with emphasis upon preferred embodiments, it will be obvious to those of ordinary skill in the art that the preferred embodiments can be varied. It is intended that the invention can be practiced otherwise than as specifically described herein. Accordingly, this invention includes all modifications encompassed within the spirit and scope of the appended claims.

What is claimed is:

1. A method of inhibiting the onset of non-TNF-α dependent inflammation, which comprises administering to a mammal exposed to an inflammation-causing condition or disease an inflammation-inhibiting effective amount of a compound of the formula:

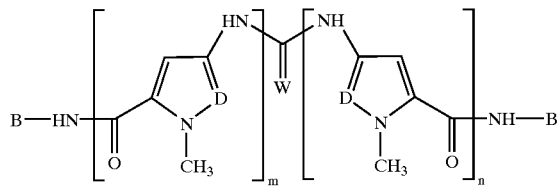

wherein m and n are the same and each is an integer of 1 to 6; W is oxygen or sulphur; each occurrence of D is independently selected and is N or CH; each of the B groups is independently selected and is (a) a saturated or an unsaturated carbocyclic ring system substituted by one or more acid groups;

(b) a saturated or an unsaturated, heteromonocyclic or heterobicyclic ring, containing one or more heteroatoms selected from the group consisting of nitrogen, oxygen and sulphur, substituted by one or more acid groups;

(c) a pyranyl or furanyl sugar residue substituted by one or more acid groups; or (d) a —CH$_2$(CHA)$_r$CH$_2$A group, wherein each A group, being the same or different, is an acid group and r is 0, 1 or 2; or a pharmaceutically acceptable salt thereof, whereupon administration of said compound or pharmaceutically acceptable salt thereof to said mammal, the onset of inflammation is inhibited.

2. The method of claim 1, wherein each of the B groups is independently selected from (a), (b) and (c), and is substituted by 1 to 3 acid groups selected from the group consisting of sulfonic acid, sulfinic acid, phosphonic acid, phosphamic acid, and carboxylic acid.

3. The method of claim 2, wherein m and n are the same and each is an integer of 2 to 4.

4. The method of claim 3, wherein all of the B groups are the same.

5. The method of claim 4, wherein all of the B groups are the same and each is a saturated or an unsaturated carbocyclic ring system substituted by one or more acid groups.

6. The method of claim 5, wherein said ring system comprises 1 to 3 rings.

7. The method of claim 6, wherein said ring system is naphthyl.

8. The method of claim 7, wherein said naphthyl ring system is substituted with 1, 2, or 3 acid groups selected from the group consisting of sulfonic acid and phosphonic acid.

9. The method of claim 2, wherein all of the B groups are the same.

10. The method of claim 9, wherein all of the B groups are the same and each is a saturated or an unsaturated carbocyclic ring system substituted by one or more acid groups.

11. The method of claim 10, wherein said ring system comprises 1 to 3 rings.

12. The method of claim 11, wherein said ring system is naphthyl.

13. The method of claim 12, wherein said naphthyl ring system is substituted with 1, 2, or 3 acid groups selected from the group consisting of sulfonic acid and phosphonic acid.

14. The method of claim 1, wherein said compound is selected from the group of compounds consisting of compounds identified by the NSC No. 645793, 645794, 651015, 651016, 651017, 658434, 662162, 668535, 668536, 668537, 664740, 664739, 670886, 670887, and 670888.

15. The method of claim 1, wherein said non-TNF-α-dependent inflammationis caused by an inflammation-causing condition or disease selected from the group consisting of allergy, asthma, blunt force trauma, reperfusion injury, non-bacteria-mediated respiratory distress syndrome, and the demyelination of nerve tissue.

16. The method of claim 1, wherein said non-TNF-α dependent inflammation is mediated through a chemokine.

17. The method of claim 16, wherein the chemokine is an α-chemokine or a β-chemokine.

18. The method of claim 17, wherein the α-chemokine is SDF-1α chemokine.

19. The method of claim 17, wherein the β-chemokine is selected from the group consisting of MIP-1α, MIP1β, HCC-1, LEC, TARC, Eotaxin and RANTES.

20. The method of claim 1, wherein said non-TNF-α dependent inflammation is mediated through a chemokine receptor.

21. The method of claim 20, wherein the chemokine receptor is an α-chemokine receptor or a β-chemmokine receptor.

22. The method of claim 21, wherein the α-chemokine receptor is CXC4.

23. The method of claim 21, wherein the β-chemokine receptor is selected from the group consisting of CCR1, CCR3, CCR5 and CCR8.

* * * * *